US007923261B2

(12) United States Patent
Colle

(10) Patent No.: US 7,923,261 B2
(45) Date of Patent: Apr. 12, 2011

(54) METHOD FOR DETERMINING A CARBON SOURCE OF A PRODUCT

(75) Inventor: Thomas H. Colle, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 2 days.

(21) Appl. No.: 12/134,888

(22) Filed: Jun. 6, 2008

(65) Prior Publication Data

US 2009/0017550 A1    Jan. 15, 2009

Related U.S. Application Data

(60) Provisional application No. 60/949,265, filed on Jul. 12, 2007.

(51) Int. Cl.
*G01N 21/76* (2006.01)
(52) U.S. Cl. ............... 436/172; 422/82.07; 422/82.08; 436/139; 436/141; 436/145; 436/164
(58) Field of Classification Search .................. None
See application file for complete search history.

(56) References Cited

U.S. PATENT DOCUMENTS

| 4,227,992 | A | * | 10/1980 | Garwood et al. ............ 208/46 |
| 4,462,686 | A | * | 7/1984 | Bridges .................... 356/318 |
| 5,714,662 | A | | 2/1998 | Vora et al. |
| 6,444,712 | B1 | | 9/2002 | Janda |
| 2003/0144565 | A1 | | 7/2003 | Allison et al. |

FOREIGN PATENT DOCUMENTS

| WO | WO01/56957 | 8/2001 |
| WO | WO2006/083409 | 8/2006 |

OTHER PUBLICATIONS

Huang et al. "An exploration of intramolecular carbon isotopic distributions of commercial acetone and isopropanol". 1999. Organic Geochemistry, vol. 30, pp. 667-674.*
Smallwood et al. "Stable carbon isotopic composition of gasolines determined by isotope ratio monitoring gas chromatography mass spectrometry". 2002. Organic Geochemistry. vol. 33, pp. 149-159.*
Fougerit et al. "Selective transformation of methanol into light olefins over a mordenite catalyst: reaction scheme and mechanism". 1999. Microporous and Mesoporous Materials. vol. 29, pp. 79-89.*
Prosser, "Fingerprinting Landfill Gas". 1998. GC Environmental, Inc.*
Polianski et al. "Collisionally assisted, highly selective laser isotope separation of carbon-13". 2004. Journal of Chemical Physics. vol. 121, No. 23, pp. 11771-11779.*
Feux, A.N. "The use of stable carbon isotopes in hydrocarbon exploration.", J. Geochem, Explor., 7 (1977), p. 155-188.
Tissot, B.P. and Welte, D.H., "Petroleum Formation and Occurrence", Springer-Verlag, 1978, p. 177-179.
J. Aali et al.; "Geochemistry and Origin of the World's Largest Gas Field from Persian Gulf, Iran," Journal of Petroleum Science and Engineering, vol. 50, pp. 161-175, 2006.
A. Stadnitskaia et al.; "Molecular and Carbon Isotopic Variability of Hydrocarbon Gases from Mud Volcanoes in the Gulf of Cadiz, NE Atlantic," Marine and Petroleum Geology, vol. 23, pp. 281-296, 2006.
Mitscherling, C. et al., "Non-invasive and isotope-selective laser-induced fluorescence spectroscopy of nitric oxide in exhaled air," J. Breath Res. 1 (2007) 026003 pp. 1-9.
Walker, D.A. et al., "A fluorescence technique for measurement of concentration in mixing liquids," J. Phys. E: Sci. Instrum. 20 (1987), pp. 217-224.

* cited by examiner

*Primary Examiner* — Yelena G Gakh
*Assistant Examiner* — David Weisz
(74) *Attorney, Agent, or Firm* — Kevin M. Faulkner

(57) ABSTRACT

This invention is directed to a method for determining a source of carbon feed used in manufacturing product produced from the carbon feed. The invention further provides a method for tracking products, particularly MTO products, derived from a particular carbon feed. In general, the method involves a variety of steps that include one or more of determining, comparing, inventorying, and tracking the $^{13}C:^{12}C$ ratio (or $HD:H_2$ ratio) of the product that is being tracked to the measured or predetermined $^{13}C:^{12}C$ ratio (or $HD:H_2$ ratio) of the feed used to make the product.

11 Claims, No Drawings

US 7,923,261 B2

METHOD FOR DETERMINING A CARBON SOURCE OF A PRODUCT

CROSS REFERENCE TO RELATED APPLICATIONS

This application claims the benefit of Provisional Application Nos. 60/949,265 filed Jul. 12, 2007, the disclosures of which are incorporated by reference in their entireties.

FIELD OF THE INVENTION

This invention relates to a method for determining a source of carbon that is ultimately used in manufacturing product produced from that carbon. This invention further relates to determining, tracking and inventorying product, particularly olefin or olefin derived products, and/or a carbon source from which the product was derived.

BACKGROUND OF THE INVENTION

Light olefins such as ethylene and propylene are important commodity petrochemicals useful in a variety of processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, are convertible into light olefins. The preferred conversion process is generally referred to as an oxygenate-to-olefin or methanol-to-olefins (both generally referred to as MTO) process, where methanol is converted to primarily ethylene and/or propylene in the presence of a molecular sieve catalyst.

There are numerous technologies available for producing methanol including fermentation or the reaction of synthesis gas (syngas) derived from a hydrocarbon feed stream. Typical feed streams for producing syngas include natural gas, petroleum liquids, coal, recycled plastics, municipal waste, as well as a variety of other organic material.

U.S. Pat. No. 5,714,662 to Vora et al. discloses integrating a methanol synthesis system with an MTO reaction system. This integration involves a combination of reforming, oxygenate production, and oxygenate conversion wherein a crude methanol stream—produced in the production of oxygenates and comprising methanol, light ends, and heavier alcohols—is passed directly to the oxygenate conversion zone for the production of light olefins. Fusel oil in the crude methanol, which typically includes higher alcohols and is generally burned as a fuel in the methanol plant, is passed to the oxygenate conversion process for additional production of light olefins.

U.S. Pat. No. 6,444,712 to Janda et al. discloses a method for the production of methanol and hydrocarbons from a methane-containing gas, such as natural gas. The method integrates a hydrocarbon synthesis unit with a methanol synthesis unit without the need to recycle unreacted syngas exiting the methanol synthesis reactor. A syngas stream and additional carbon dioxide from the hydrocarbon synthesis unit are combined to form an optimal syngas composition for methanol and hydrocarbon synthesis.

It would be desirable to better understand how the integration of various facilities with the MTO process affects product quality. For example, it would be desirable to understand how various oxygenate feeds to the MTO facility affect the quality of a variety of downstream products such as olefins and (co)polymers that are derived from the olefins produced in the MTO process. Accordingly, it would be desirable to establish a method that could be used to track products, particularly MTO products, derived from a particular carbon feed source. In other words, it would be desirable to be able to readily determine from which carbon source a carbon product has been derived.

SUMMARY OF THE INVENTION

This invention provides a method for tracking products, particularly MTO products, derived from a particular carbon feed. In general, the method involves a variety of steps that involve one or more of determining, comparing, inventorying, and tracking the $^{13}C:^{12}C$ ratio (or $HD:H_2$ ratio) of the product that is being tracked to the measured or predetermined $^{13}C:^{12}C$ ratio (or $HD:H_2$ ratio) of the feed used to make the product.

According to one aspect of the invention, there is provided a method for determining a source of carbon feed used in manufacturing product produced from the carbon feed. The method includes providing a sample of the product produced from the carbon feed; determining $^{13}C:^{12}C$ ratio of the product; and comparing the $^{13}C:^{12}C$ ratio of the product to a predetermined $^{13}C:^{12}C$ ratio.

According to another aspect of the invention, there is provided a method for determining a source of carbon feed used in manufacturing product produced from the carbon feed, that includes the steps of providing a sample of the carbon feed; determining $^{13}C:^{12}C$ ratio of the carbon feed; providing a sample of product produced from the carbon feed; determining $^{13}C:^{12}C$ ratio of the product; and comparing the $^{13}C:^{12}C$ ratio of the product to the $^{13}C:^{12}C$ ratio of the carbon feed.

As yet another aspect of the invention, there is provided a method for determining a source of carbon feed used in manufacturing polymers. The method includes the steps of providing a sample of the carbon feed; determining $^{13}C:^{12}C$ ratio of the carbon in the feed; providing a sample of olefin-containing polymer produced from the carbon feed; determining $^{13}C:^{12}C$ ratio of the olefin-containing polymer; and comparing the $^{13}C:^{12}C$ ratio of the olefin-containing polymer to the $^{13}C:^{12}C$ ratio of the carbon in the feed.

Another aspect of the invention is directed to a method for determining a source of hydrocarbon feed used in manufacturing product produced from the hydrocarbon feed. The method includes one or more of the steps of providing a sample of the product produced from the carbon feed; determining $HD:H_2$ ratio of the product; and comparing the $HD:H_2$ ratio of the product to a predetermined $HD:H_2$ ratio.

In a preferred embodiment of one or more aspects of the invention, the compared product that falls within a range of ±5% of the predetermined ratio is tracked. Preferably, the tracked product is sent to inventory.

In another preferred embodiment of the invention, the product comprises olefin or olefin-containing polymer. In still another, the carbon or hydrocarbon feed comprises methane from natural gas.

According to another aspect of the invention, a method for determining whether product inventory contains product made from methane from natural gas is provided. The method includes one or more of the steps of providing a sample of the natural gas, wherein the natural gas contains the methane; providing a sample of the product inventory; determining $^{13}C:^{12}C$ ratio of the sample of the natural gas; determining $^{13}C:^{12}C$ ratio of the sample of the product inventory; comparing the $^{13}C:^{12}C$ ratio of the methane to the $^{13}C:^{12}C$ ratio of the product inventory; and determining whether product inventory contains product made from the methane from the natural gas based on the comparison of the $^{13}C:^{12}C$ ratio of the methane to the $^{13}C:^{12}C$ ratio of the product inventory.

Another aspect of the invention involves a method for determining whether product inventory contains product made from methane from natural gas. The method includes one or more of the steps of providing a sample of the natural gas, wherein the natural gas contains the methane; providing a sample of an olefin-containing polymer product inventory; determining $^{13}C:^{12}C$ ratio of the sample of the natural gas; determining $^{13}C:^{12}C$ ratio of the sample of the olefin-containing polymer product inventory; comparing the $^{13}C:^{12}C$ ratio of the methane to the $^{13}C:^{12}C$ ratio of the polyolefin product inventory; and determining whether product inventory contains product made from the methane from the natural gas based on the comparison of the $^{13}C:^{12}C$ ratio of the methane to the $^{13}C:^{12}C$ ratio of the olefin-containing polymer product inventory.

Another aspect of the invention provides for a method for determining hydrocarbon source of product inventory that includes providing a sample of product from the product inventory, and determining $$\delta(^{13}C)=(R'_{sample}/R'_{standard}-1)\times1000$$

wherein $R'_{sample}$ is the ratio of $^{13}C$ to $^{12}C$ in the provided sample of product from the product inventory. From the value of $\delta(^{13}C)$ it is determined whether the product contains hydrocarbon from geologic methane based on the value of $\delta(^{13}C)$. In one embodiment, the $\delta(^{13}C)$ value is not greater than −36. In another embodiment, the $\delta(^{13}C)$ value is at least −60.

Another aspect of the invention provides for a method for determining hydrocarbon source of product inventory that includes providing a sample of product from the product inventory; and determining $$\delta(deuterium)=(R''_{sample}/R''_{standard}-1)\times1000$$

wherein $R''_{sample}$ is the HD:$H_2$ ratio in the provided sample of product from the product inventory. From the value of $\delta(deuterium)$, it is determined whether the product contains hydrocarbon from geologic methane based on the value of $\delta(deuterium)$. In one embodiment, the $\delta(deuterium)$ value is not greater than −250. In another embodiment, the value of $\delta(deuterium)$ is at least −450.

Another aspect of the invention involves determination of patent infringement using one or more of the methods. In one embodiment, infringement can be determined on the basis of whether olefin or olefin-containing polymer is manufactured or derived from methane from natural gas. In a particular embodiment, the method includes obtaining a sample of olefin or olefin-containing polymer; and determining hydrocarbon source of the olefin or olefin-containing polymer based upon a $\delta(^{13}C)$ value or a $\delta(deuterium)$ value.

DETAILED DESCRIPTION OF THE INVENTION

I. Isotopic Ratio of the Product Indicates the Feed Source

This invention is directed to a method for determining a source of carbon feed used in manufacturing product produced from the carbon feed. In general, the method involves providing a sample of the product produced from the carbon feed, and determining the isotopic ratio, e.g., the $^{13}C:^{12}C$ ratio or the HD:$H_2$ (deuterium:hydrogen) ratio of the product.

In one embodiment, the $^{13}C:^{12}C$ ratio of the product is compared to a predetermined or measured $^{13}C:^{12}C$ ratio. When the ratio of the compared product falls within a range around the predetermined ratio, then the product can be tracked on the basis of the carbon source from which it was derived. Preferably, the tracked product has a ratio that falls within a range of ±5% of the predetermined or measured ratio.

The $^{13}C:^{12}C$ ratio of the product will generally indicate the ultimate carbon source. For example, methane from natural gas tends to have a lower $^{13}C:^{12}C$ ratio than heavier hydrocarbons such as ethane, propane, petroleum feed fractions, and coal. The products produced from the methane from natural gas should also reflect the lower $^{13}C:^{12}C$ ratio. Therefore, comparing the $^{13}C:^{12}C$ ratio of the product produced to a known or standard $^{13}C:^{12}C$ ratio should indicate from which carbon source the product was derived.

The product can be further analyzed for quality to determine whether different carbon feed sources affect the quality. The product can also be easily tracked based on its $^{13}C:^{12}C$ ratio. For example, when the product is determined to be within a certain $^{13}C:^{12}C$ ratio, it can be easily tracked and sent to inventory in a location, as desired.

According to one aspect of the invention, the $^{13}C:^{12}C$ ratio of the product can be compared to a predetermined $^{13}C:^{12}C$ ratio. The $^{13}C:^{12}C$ ratio is reflective of the actual ratio of any known carbon-based compound.

In another embodiment, the HD:$H_2$ ratio of the hydrocarbon product can be compared to a predetermined or measured HD:$H_2$ ratio. When the ratio of the compared hydrocarbon product falls within the predetermined ratio, then the product can be tracked on the basis of the hydrocarbon source from which it was derived. Preferably, the tracked product has a ratio that falls within a range of ±5% of the predetermined or measured ratio.

As with the $^{13}C:^{12}C$ ratio, the HD:$H_2$ ratio of the product generally indicates the ultimate hydrocarbon source. For example, methane from natural gas tends to have a lower HD:$H_2$ ratio than heavier hydrocarbons such as ethane, propane, petroleum feed fractions, and coal. The products produced from the methane from natural gas should thus reflect the lower HD:$H_2$ ratio. Therefore, comparing the HD:$H_2$ ratio of the product produced to a known or standard HD:$H_2$ ratio should indicate from which hydrocarbon source the product was derived.

The product can be further analyzed for quality to determine whether different hydrocarbon feed sources affect the quality. The product can also be easily tracked based on its HD:$H_2$ ratio. For example, when the product is determined to be within a certain HD:$H_2$ ratio, it can be easily tracked and sent to inventory in a location, as desired.

According to one aspect of the invention, the HD:$H_2$ ratio of the product can be compared to a predetermined HD:$H_2$ ratio. The HD:$H_2$ ratio is reflective of the actual ratio of any known hydrocarbon.

In one embodiment, the isotopic ratio can be used to determine deviations or divergence from a standard ratio. An example of the carbon isotope deviation is provided by the following formula:

$$\delta(^{13}C)=(R'_{sample}/R'_{standard}-1)\times1000$$

where $R'_{sample}$ is the ratio of $^{13}C$ to $^{12}C$ in the sample of the material being tested; and $R'_{standard}$ is the ratio of the natural abundance of $^{13}C$ to the natural abundance of $^{12}C$ for a reference material (which is equal to 0.01109/0.98891).

In essence, the carbon isotope deviation is the fractional difference between a sample and the standard; only here, it is actually a per mil (‰) difference rather than a percent (%)

difference, since the values tend to be so small. Looking at the above equation, it can be seen that, if a sample has a greater proportion of the heavier isotope of carbon, $^{13}C$, then it will have a positive $\delta(^{13}C)$ value and, if it is depleted in the heavier isotope, then it will have a negative $\delta(^{13}C)$ value.

In one embodiment of the invention, a sample can be analyzed to determine the presence of carbon that is derived from geologic methane. In a particular embodiment, the sample containing carbon from geologic methane can have a $\delta(^{13}C)$ value of not greater than −36. In another embodiment, the sample containing carbon from geologic methane can have a $\delta(^{13}C)$ value of at least −60.

In another embodiment, the $HD:H_2$ ratio of the product can be compared to a predetermined or measured $HD:H_2$ ratio. When the ratio of the compared product falls within the predetermined ratio, the product can then be tracked on the basis of the hydrogen or hydrocarbon source from which it was derived. Preferably, the tracked product has a ratio that falls within a range of ±5% of the predetermined or measured ratio.

The $HD:H_2$ ratio of the product generally indicates the ultimate hydrogen source or hydrocarbon. For example methane from natural gas tends to have a lower $HD:H_2$ ratio than heavier hydrocarbons such as ethane, propane, petroleum feed fractions, and coal. The products produced from the methane from natural gas should thus reflect the lower $HD:H_2$ ratio. Therefore, comparing the $HD:H_2$ ratio of the product produced to a known or standard $HD:H_2$ ratio should indicate from which hydrocarbon source the product was derived.

The product can be further analyzed for quality to determine whether different hydrocarbon feed sources affect the quality. The product can also be easily tracked based on its $HD:H_2$ ratio. For example, when the product is determined to be within a certain $HD:H_2$ ratio, it can be easily tracked and sent to inventory in a location, as desired.

According to one aspect of the invention, the $HD:H_2$ ratio of the product can be compared to a predetermined $HD:H_2$ ratio. The $HD:H_2$ ratio is reflective of the actual ratio of any known carbon-based.

In one embodiment, the isotopic ratio can be used to determine deviations or divergence from a standard ratio. An example of the carbon isotope deviation is provided by the following formula:

$$\delta(\text{deuterium}) = (R''_{sample}/R''_{standard} - 1) \times 1000$$

where $R''_{sample}$ is the $HD:H_2$ ratio in the sample of the material being tested; and $R''_{standard}$ is the ratio of the natural abundance of deuterium to the natural abundance of hydrogen for a reference material (which is equal to 0.00015/0.99985).

Thus, if a sample has a greater proportion of the heavier isotope of hydrogen, i.e., deuterium, then it will have a positive $\delta(\text{deuterium})$ value and if it is depleted in the heavier isotope, then it will have a negative $\delta(\text{deuterium})$ value.

In one embodiment of the invention, a sample can be analyzed to determine the presence of hydrocarbon that is derived from geologic methane. In a particular embodiment, the sample containing hydrocarbon from geologic methane can have a $\delta(\text{deuterium})$ value of not greater than −250. In another embodiment, the sample containing carbon from geologic methane can have a $\delta(\text{deuterium})$ value of at least −450.

According to another aspect of the invention, a sample of a particular carbon feed can be provided. The $^{13}C:^{12}C$ ratio of the carbon in the feed can then be determined. The $^{13}C:^{12}C$ ratio of the product can then be determined and the two compared to determine if the two ratios are substantially similar, meaning whether the carbon in the product and that of the carbon source look to be of the same origin. This invention can be particularly useful in determining if the various products produced in an oxygenate-to-olefin process or methanol-to-olefin process are ultimately derived from methane recovered from natural gas. Since such methane has a readily identifiable $^{13}C:^{12}C$ ratio, a product derived from that methane should have substantially the same $^{13}C:^{12}C$ ratio.

II. Methods of Determining Isotope Ratios

Any technique for quantitatively or qualitatively determining isotopic composition can be used to determine the $^{13}C:^{12}C$ ratio. For example, certain types of isotope ratio determinations are commonly done on mass spectrometers that have been specifically designed for that purpose. Mass spectrometers can determine the isotopic ratios of a limited number of gases: $H_2$, $N_2$, $CO_2$ (for $^{13}C:^{12}C$ and $^{18}O:^{16}O$ ratios), $SO_2$, and $SF_6$, inter alia. Therefore, when it is desired to determine the isotopic ratios of other compounds, the compound of interest can typically be converted to the appropriate gas and the isotopic ratio determined by a mass spectrometer (MS). Determination of $HD/H_2$ and $^{13}C:^{12}C$ ratios in organic compounds generally includes combustion of the sample to $CO_2$ and water, separation of the water from the $CO_2$, and conversion of the water over hot metal shavings (e.g., U, Zn, Cr, or Mn). In some cases, organic hydrogen can be directly converted to elemental hydrogen by pyrolysis over hot metal shavings (e.g., Cr or Mn). The resulting gases then can be analyzed on the mass spectrometer.

In measuring a specific isotopic ratio of natural hydrocarbon gases, the gas mixture can preferably be separated into its individual compounds. In one embodiment, this can preferably be accomplished by means of a gas chromatograph (GC), e.g., using helium as a carrier gas. The separated gases can preferably be flowed into a furnace (preferably about 800° C. to about 1000° C.) packed with metal (copper) oxide, where the individual gases are converted to $CO_2$ and water. Once the separated compounds have emerged at the end of the furnace, the isotopic composition of the individual compounds can be determined.

In one embodiment of the invention, the $CO_2$ and water from the individual compounds can be diverted into individual detachable cold traps and frozen. Once the components have been collected, the cold traps can be transferred to a purification line, where the carrier gas (helium) can be pumped out and the $CO_2$ can cryogenically be separated from the water. The pure $CO_2$ can then be cryogenically trapped in a transfer tube and transferred to the MS, where the $^{13}CO_2:^{12}CO_2$ ratio can be determined. The water can be transferred into a reduction tube for conversion to hydrogen gas, which can then be analyzed by the MS for $HD:H_2$ ratios.

In another embodiment, (generally referred to as GCIRMS-GC Isotope Ratio Mass Spectrometry) the system can be adapted to analyze either $CO_2$ or hydrogen, preferably $CO_2$. For $CO_2$, at the end of the furnace the carrier gas (helium)/$CO_2$/$H_2O$ mixture can be passed through a water trap. Then, the carrier gas (helium)/$CO_2$ mixture can be injected into the mass spectrometer, where the $^{13}CO_2:^{12}CO_2$ ratio can be determined. This method typically requires significantly smaller samples; however the duration of the $^{13}CO_2:^{12}CO_2$ ratio determination is typically much shorter (the width of the GC peak), resulting in less accurate ratios. The duration of the complete analysis (methane to pentane) can be determined by length of time required to elute all the components through the GC. In order to determine the $HD/H_2$ ratio, the water trap can be removed and the metal (copper) oxide tube furnace replaced by a pyrolysis tube furnace, where the gases can be converted to elemental carbon and hydrogen gas. The hydrogen gas can then be analyzed with the appropriate tuning of the MS in a similar fashion to $CO_2$.

In another embodiment of the invention, isotopic ratios can be measured via quantum vibrational transition. The measurements can be based on emission spectra or absorption spectra, whichever is desired.

In another embodiment, isotopic composition of individual hydrocarbons in a fluid can be determined based on the different optical properties of individual hydrocarbons with and without heavy atom ($^{13}C$ and D) substitution on the molecule. In this embodiment, measurements can be made directly on the gas of interest without the need to first convert it to $CO_2$ and/or $H_2$ and without the need remove other hydrocarbon and non-hydrocarbon gases from the mixture.

Examples of determination of isotopic composition based on optical properties include, but are not limited to, Laser Induced Florescence (LIF) and detection based on changes in laser beam intensity (absorption). The lasers can be continuous wave or pulsed. Semiconducting diode lasers are preferred for certain industrial purposes and are readily commercially available. Any number of other types of lasers, however, can be used, including gas lasers, excimer lasers, and dye lasers. Lasers can be chosen based on characteristics of power, polarization, coherency, bandwidth, stability, Q-switch repetition rate, wavelength regime, and maintenance considerations. Semiconducting diode lasers are preferred, in certain circumstances because they tend to require little maintenance. They have large power capabilities, have narrow bandwidths, and are typically very stable, making them most attractive to industry. A laser with a high repetition rate (around 10 KHz), with a 3% shot to shot stabilization or less, and which is tunable over the absorption band of hydrocarbons fundamental vibrational modes is particularly preferred. Multiple lasers may be employed, e.g., if a combination of lasers covers the entire wavelength regions of interest.

In one embodiment of the invention, a sample of carbon source or product made from a carbon source can be converted to carbon dioxide. This can preferably be accomplished by combustion of the carbon material in an excess of oxygen. For small samples of a material, such as natural gas, this can be accomplished by passage of the sample or components thereof through a flame ionization detector, which is an instrument conventionally used for quantitative analysis of a hydrocarbon component of a sample by combustion of the sample components in a hydrogen-rich flame and for detection of selected ions produced by the combustion.

In another embodiment, the effluent from the flame ionization detector, which typically includes carbon dioxide and water, can be analyzed for the relative amounts of isotopes of carbon present. This can be accomplished by any means capable of determining the isotope composition, such as by an isotope ratio mass spectrometer. The effluent can be treated prior to carbon isotope analysis for removal of undesired components, which generally includes water and inert gases.

In yet another embodiment of the invention, the sample to be analyzed can be sent to a separation step for obtaining a desired constituent or group of constituents from the sample. The separation of a gaseous sample can be effected, e.g., using gas chromatography, from which the desired constituents can be passed to the flame ionization detector and to the mass spectrometer.

The samples which can be analyzed by the invention method can include any carbon-containing material that can be oxidized with good efficiency to carbon dioxide. Hydrocarbon materials are particularly suitable.

III. MTO Products to be Tracked

The carbon products to be tracked according to this invention are preferably products from an oxygenate-to-olefins or methanol-to-olefins reaction system (both systems generally referred to herein as MTO). In this system, a feed stream to the MTO system can be contacted with an olefin-forming catalyst to form an olefin product. The olefin products can then be converted to a variety of other products, including polyolefins. Any of these olefin or other conversion products can be tracked according to this invention by determining the isotopic ratio and by comparing that ratio to a reference ratio to determine the ultimate carbon source from which the product was made. For example, the $^{13}CO_2:^{12}CO_2$ ratio and/or the $HD/H_2$ ratio of the product can be determined, and that ratio compared to a known or determined value for a variety of carbon sources. The ratios of the carbon source to the product derived from that same source should be substantially the same.

The feed stock sent to the MTO system can be converted primarily into one or more olefins. The olefins or olefin monomers produced from the feedstock typically have from 2 to 30 carbon atoms, preferably 2 to 8 carbon atoms, more preferably 2 to 6 carbon atoms, most preferably 2 to 4 carbons atoms, and particularly ethylene and/or propylene. Non-limiting examples of olefin monomers include, but are not limited to, ethylene, propylene, butene-1, pentene-1,4-methyl-pentene-1, hexene-1, octene-1, decene-1, and isomers thereof, preferably ethylene, propylene, butene-1, pentene-1, 4-methyl-pentene-1, hexene-1, octene-1, and isomers thereof. Other olefin monomers can include unsaturated monomers, diolefins having 4 to 18 carbon atoms, conjugated or nonconjugated dienes, polyenes, vinyl monomers, and cyclic olefins, inter alia.

In a preferred embodiment, the feedstock, preferably one or more oxygenates, can be converted in the presence of a molecular sieve catalyst composition into olefin(s) having 2 to 6 carbons atoms, preferably 2 to 4 carbon atoms. Most preferably, the olefin(s), alone or in combination, can be converted from a feedstock containing an oxygenate, preferably containing an alcohol, more preferably containing methanol, to the preferred olefin(s) ethylene and/or propylene.

In one embodiment of the invention, an olefin stream can be obtained by contacting oxygenate with a molecular sieve catalyst. The oxygenate can comprise at least one organic compound containing at least one oxygen atom, such as aliphatic alcohols, ethers, carbonyl compounds (aldehydes, ketones, carboxylic acids, carbonates, esters, and the like), and the like. When the oxygenate comprises an alcohol, the alcohol includes an aliphatic moiety having from 1 to 10 carbon atoms, more preferably from 1 to 4 carbon atoms. Representative alcohols include, but are not necessarily limited to, lower straight- and branched-chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds can include methanol, dimethyl ether, and a mixture thereof.

Molecular sieves capable of converting an oxygenate to an olefin compound include zeolites as well as non-zeolites, and are of the large-, medium-, or small-pore type. Small-pore molecular sieves are preferred in one embodiment of this invention, however. As defined herein, small-pore molecular sieves have a pore size of less than about 5.0 angstroms.

Generally, suitable catalysts have a pore size ranging from about 3.5 to about 5.0 angstroms, preferably from about 4.0 to about 5.0 angstroms, and most preferably from about 4.3 to about 5.0 angstroms.

Zeolite materials, both natural and synthetic, have been demonstrated to have catalytic properties for various types of hydrocarbon conversion processes. In addition, zeolite materials have been used as adsorbents, as catalyst carriers for various types of hydrocarbon conversion processes, and in other applications. Zeolites are complex crystalline aluminosilicates which form a network of $AlO_2^-$ and $SiO_2$ tetrahedra linked by shared oxygen atoms. The negativity of the tetrahedra can be balanced by the inclusion of cations, such as alkali or alkaline earth metal ions. In the manufacture of some zeolites, non-metallic cations, such as tetramethylammonium (TMA) or tetrapropylammonium (TPA), can be present during synthesis. The interstitial spaces or channels formed by the crystalline network enable zeolites to be used as molecular sieves in separation processes, as catalysts for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

One type of olefin-forming catalyst capable of producing large quantities of ethylene and propylene is a silicoaluminophosphate (SAPO) molecular sieve. Silicoaluminophosphate molecular sieves are generally classified as being microporous materials having 8-, 10-, or 12-membered ring structures. These ring structures can have an average pore size ranging from about 3.5 to about 15 angstroms. Preferred are the small-pore SAPO molecular sieves having an average pore size of less than about 5 angstroms, preferably an average pore size ranging from about 3.5 to about 5 angstroms, more preferably from about 3.5 to about 4.2 angstroms. These pore sizes are typical of molecular sieves having 8-membered rings.

To convert oxygenate to olefin(s), any variety of reactor systems can be used, including fixed bed, fluid bed, and moving bed systems. Preferred reactors of one embodiment are co-current riser reactors and short-contact-time countercurrent free-fall reactors. The reactor is preferably one in which an oxygenate feedstock can be contacted with a molecular sieve catalyst at a weight hourly space velocity (WHSV) of at least about 1 $hr^{-1}$, preferably in the range of from about 1 $hr^{-1}$ to 1000 $hr^{-1}$, for in the range of from about 20 $hr^{-1}$ to about 1000 $hr^{-1}$ or in the range of from about 30 $hr^{-1}$ to about 500 $hr^{-1}$. WHSV is defined herein as the weight of oxygenate, and reactive hydrocarbon which may optionally be in the feed, per hour per weight of the molecular sieve in the reactor. Because the catalyst or the feedstock may contain other materials that act as inerts or diluents, the WHSV is calculated on the weight basis of the oxygenate feed, and any reactive hydrocarbon which may be present with the oxygenate feed, and the molecular sieve contained in the reactor.

Preferably, the oxygenate feed can be contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., preferably from about 300° C. to about 600° C. or from about 350° C. to about 550° C. At the lower end of the temperature range, the formation of the desired olefin products may become markedly slow, with a relatively high content of oxygenated olefin byproducts being found in the olefin product. However, the selectivity to ethylene and propylene at reduced temperatures may be increased. At the upper end of the temperature range, the process may not form an optimum amount of ethylene and propylene product, but the conversion of oxygenate feed will generally be high.

Operating pressure also may vary over a wide range, including autogenous pressures. Effective pressures include, but are not necessarily limited to, a total pressure of at least 1 psia (7 kPa), preferably at least about 5 psia (34 kPa). The process is particularly effective at higher total pressures, including a total pressure of at least about 20 psia (138 kPa). Preferably, the total pressure is at least about 25 psia (172 kPa), more preferably at least about 30 psia (207 kPa). For practical design purposes it is desirable to use methanol as the primary oxygenate feed component and to operate the reactor at a pressure of not greater than about 500 psia (3445 kPa), preferably not greater than about 400 psia (2756 kPa) or not greater than about 300 psia (2067 kPa).

Undesirable byproducts can be avoided by operating at an appropriate gas superficial velocity. As the gas superficial velocity increases, the conversion typically decreases, avoiding undesirable byproducts. As used herein, the term, "gas superficial velocity" is defined as the combined volumetric flow rate of vaporized feedstock, which includes diluent when present in the feedstock, as well as conversion products, divided by the cross-sectional area of the reaction zone. Because the oxygenate is converted to a product having significant quantities of ethylene and propylene while flowing through the reaction zone, the gas superficial velocity may vary at different locations within the reaction zone. The degree of variation can depend on the total number of moles of gas present, the cross-section of a particular location in the reaction zone, the temperature, the pressure, and other relevant reaction parameters.

In one embodiment, the gas superficial velocity can be maintained at a rate of greater than 1 meter per second (m/s) at least one point in the reaction zone. In another embodiment, it is desirable that the gas superficial velocity can be greater than about 2 m/s at at least one point in the reaction zone. More desirably, the gas superficial velocity can be greater than about 2.5 m/s, greater than about 4 m/s, or even greater than about 8 m/s at least one point in the reaction zone.

The ethylene and propylene streams that are also separated according to this invention can be polymerized to form plastic compositions, e.g., polyolefins, particularly polyethylene and polypropylene, as well as copolymers of two or more of ethylene, propylene, $C_{4+}$ olefins, and optionally other non-olefin comonomers, and these materials can be tracked according to the invention. Any of a variety of processes for forming polyethylene or polypropylene can be used. Catalytic processes are preferred. Particularly preferred are metallocene, Ziegler/Natta, aluminum oxide, and acid catalytic systems. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Preferably, the polyolefin forming process is carried out at a temperature ranging between about 50° C. and about 320° C. The reaction can be carried out at low, medium, or high pressure, being anywhere within the range of about 1 bar to about 3200 bar. For processes carried out in solution, an inert diluent can be used. In this type of operation, it is preferred that the pressure be at a range of from about 10 bar to about 150 bar, and more preferably at a temperature range of from about 120° C. to about 250° C. For gas-phase processes, it is preferred that the temperature generally be within a range of about 60° C. to 120° C. and that the operating pressure be from about 5 bar to about 50 bar.

In addition to polyolefins, numerous other olefin derivatives may be formed from the ethylene, propylene, and $C_{4+}$ olefins, particularly butylene, separated according to this invention. The olefins separated according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_{12}$ mono carboxylic acids and the $C_1$-$C_{12}$ mono alcohols, linear alpha olefins, vinyl acetate, ethylene dichloride and vinyl chloride, ethylbenzene, ethylene oxide, cumene, acrolein, allyl chloride, propylene oxide, acrylic acid, ethylene-propylene rubbers, acrylonitrile, and trimers and dimers of ethylene and propylene. The $C_{4+}$ olefins, butylene in particular, are particularly suited for the manufacture of aldehydes, acids, alcohols, and esters made from $C_5$-$C_{13}$ mono carboxylic acids. Any of these products can also be tracked according to this invention.

IV. Carbon Sources Useful in the MTO Process

Carbon sources that can be used as the ultimate feed source in the MTO process can be derived from a variety of carbon sources. Non-limiting examples of such sources include biomass, natural gas, $C_1$-$C_5$ hydrocarbons, naphtha, heavy petroleum oils, coke (i.e., coal), and the like, and combinations thereof. Preferably, the carbon source is from a natural gas source. The methane is preferably recovered from the natural gas source in a quantity that includes methane in an amount of at least about 50% by volume, more preferably at least about 70% by volume, most preferably at least about 80% by volume.

One way of converting the carbon source to a feed composition for the MTO process is first to convert the carbon source to synthesis gas (syngas), and then to convert the syngas to a methanol-containing composition, with the methanol-containing composition being used as feed for the MTO process. Any process suitable for converting syngas to a methanol composition can be used. Such processes can be catalytic and typically entail the use of carbon oxide conversion catalysts to convert the syngas to the methanol composition. In one embodiment, the carbon oxide conversion catalyst can be a copper-containing catalyst.

Syngas is defined as a gas comprising primarily carbon monoxide (CO), carbon dioxide ($CO_2$) and hydrogen ($H_2$). Optionally, syngas may also include methane ($CH_4$), and small amounts of ethane and propane. Non-limiting examples of processes for converting carbon components to syngas include steam reforming, partial oxidation, and autothermal reforming.

The carbon source used in the conversion of the carbon material to synthesis gas can optionally be treated to remove impurities that can cause problems in further processing of the hydrocarbon feed stream. These impurities can poison many conventional propylene and ethylene forming catalysts. A majority of the impurities, which may be present, can be removed in any desirable manner. The carbon source can preferably be purified to remove sulfur compounds, nitrogen compounds, particulate matter, other condensables, and/or other potential catalyst poisons prior to being converted into synthesis gas.

In one embodiment of the invention, the carbon source can be passed to a synthesis gas plant. Synthesis gas produced in this plant can be sent to a methanol synthesis process for conversion to a methanol composition. The methanol synthesis gas process can be accomplished in the presence of a methanol synthesis catalyst.

In one embodiment, the synthesis gas can be sent as is to the methanol synthesis process. In another embodiment, the hydrogen, carbon monoxide, and/or carbon dioxide content of the synthesis gas can be adjusted for efficiency of conversion. Preferably, the synthesis gas input to the methanol synthesis reactor can have a molar ratio of hydrogen ($H_2$) to carbon oxides ($CO+CO_2$) in the range from about 0.5:1 to about 20:1, more preferably in the range from about 2:1 to about 10:1. In another embodiment, the synthesis gas can have a molar ratio of hydrogen ($H_2$) to carbon monoxide (CO) of at least 2:1. Carbon dioxide can optionally be present in an amount of not greater than 50% by weight, based on total weight of the synthesis gas.

Preferably, the stoichiometric molar ratio can be sufficiently high so as maintain a high yield of methanol, but also preferably not so high as to reduce the volume productivity of methanol. More preferably, the synthesis gas fed to the methanol synthesis can have a stoichiometric molar ratio (i.e., a molar ratio of $H_2:(2CO+3CO_2)$) from about 1.0:1 to about 2.7:1, more preferably from about 1.1 to about 2.0 or from about 1.2:1 to about 1.8:1.

The $CO_2$ content, relative to that of CO, in the synthesis gas should be high enough so as to maintain an appropriately high reaction temperature and preferably to minimize the amount of undesirable by-products such as paraffins. At the same time, the relative $CO_2$ to CO content should not be too high so as to reduce methanol yield. Preferably, the synthesis gas contains $CO_2$ and CO at a ratio from about 0.5 to about 1.2, more preferably from about 0.6 to about 1.0.

In one embodiment, the catalyst used in the methanol synthesis process can include an oxide of at least one element selected from the group consisting of copper, silver, zinc, boron, magnesium, aluminum, vanadium, chromium, manganese, gallium, palladium, osmium, and zirconium. Preferably, the catalyst can be a copper-based catalyst, more preferably containing a copper oxide.

Additionally or alternately, the invention can be described by reference to the following embodiments.

Embodiment 1

A method for determining a source of carbon feed used in manufacturing product produced from the carbon feed, comprising: providing a sample of the product produced from the carbon feed; determining $^{13}C:^{12}C$ ratio of the product; and comparing the $^{13}C:^{12}C$ ratio of the product to a predetermined $^{13}C:^{12}C$ ratio.

Embodiment 2

A method for determining a source of carbon feed used in manufacturing product produced from the carbon feed, comprising: providing a sample of the carbon feed; determining $^{13}C:^{12}C$ ratio of the carbon feed; providing a sample of product produced from the carbon feed; determining $^{13}C:^{12}C$ ratio of the product; and comparing the $^{13}C:^{12}C$ ratio of the product to the $^{13}C:^{12}C$ ratio of the carbon feed.

Embodiment 3

A method for determining a source of carbon feed used in manufacturing polymers, comprising: providing a sample of the carbon feed; determining $^{13}C:^{12}C$ ratio of the carbon in the feed; providing a sample of olefin-containing polymer produced from the carbon feed; determining $^{13}C:^{12}C$ ratio of the olefin-containing polymer; and comparing the $^{13}C:^{12}C$ ratio of the olefin-containing polymer to the $^{13}C:^{12}C$ ratio of the carbon in the feed.

Embodiment 4

A method for determining whether product inventory contains product made from methane from natural gas, comprising: providing a sample of the natural gas, wherein the natural gas contains the methane; providing a sample of the product inventory; determining $^{13}C:^{12}C$ ratio of the sample of the natural gas; determining $^{13}C:^{12}C$ ratio of the sample of the product inventory; comparing the $^{13}C:^{12}C$ ratio of the methane to the $^{13}C:^{12}C$ ratio of the product inventory; and determining whether product inventory contains product made from the methane from the natural gas based on the comparison of the $^{13}C:^{12}C$ ratio of the methane to the $^{13}C:^{12}C$ ratio of the product inventory.

Embodiment 5

A method for determining a source of hydrocarbon feed used in manufacturing product produced from the hydrocarbon feed, comprising: providing a sample of the product produced from the carbon feed; determining $HD:H_2$ ratio of the product; and comparing the $HD:H_2$ ratio of the product to a predetermined $HD:H_2$ ratio.

Embodiment 6

The method of any of the previous embodiments, further comprising tracking the compared product that falls within a range of from ±5% of the predetermined ratio.

Embodiment 7

The method of embodiment 6, further comprising sending the tracked product to inventory.

Embodiment 8

The method of any of the embodiments 1-2 and 4-7, wherein the product comprises olefin or olefin-containing polymer.

Embodiment 9

The method of any of the previous embodiments, wherein the carbon feed comprises methane from natural gas.

Embodiment 10

A method for determining hydrocarbon source of product inventory, comprising: providing a sample of product from the product inventory; determining $$\delta(^{13}C) = (R'_{sample}/R'_{standard} - 1) \times 1000$$

wherein $R'_{sample}$ is the ratio of $^{13}C$ to $^{12}C$ in the provided sample of product from the product inventory; and determining whether the product contains hydrocarbon from geologic methane based on the value of $\delta(^{13}C)$.

Embodiment 11

The method of embodiment 10, wherein $\delta(^{13}C)$ is not greater than −36.

Embodiment 12

The method of embodiment 10, wherein $\delta(^{13}C)$ is at least −60.

Embodiment 13

A method for determining hydrocarbon source of product inventory, comprising: providing a sample of product from the product inventory; determining $$\delta(deuterium) = (R''_{sample}/R''_{standard} - 1) \times 1000$$

wherein $R'_{sample}$ is the $HD:H_2$ ratio in the provided sample of product from the product inventory; and determining whether the product contains hydrocarbon from geologic methane based on the value of $\delta(deuterium)$.

Embodiment 14

The method of embodiment 13, wherein $\delta(deuterium)$ is not greater than −250.

Embodiment 15

The method of embodiment 13, wherein $\delta(deuterium)$ is at least −450.

Embodiment 16

A method of detecting infringement of a patent, comprising: obtaining a sample of olefin or olefin-containing polymer; and determining hydrocarbon source of the olefin or polyolefin based upon a $\delta(^{13}C)$ value or a $\delta(deuterium)$ value.

The principles and modes of operation of this invention have been described above with reference to various exemplary and preferred embodiments. As understood by those of skill in the art, the overall invention, as defined by the claims, encompasses other preferred embodiments not specifically enumerated herein.

What is claimed is:

1. A method for determining a source of carbon feed used in manufacturing product produced from the carbon feed, comprising:
   providing a feed stream of an oxygenate to an MTO system and contacting the feed stream with an olefin-forming catalyst to form an olefin product;
   providing a sample of the product produced from the carbon feed;
   directly determining $^{13}C:^{12}C$ ratio of the product by Laser Induced Florescence (LIF) without the need to first convert it to $CO_2$ and/or $H_2$; and comparing the $^{13}C:^{12}C$ ratio of the product to a predetermined $^{13}C:^{12}C$ ratio from the source.

2. The method of claim 1, further comprising tracking the compared product that falls within a range of from ±5% of the predetermined ratio.

3. The method of claim 1, wherein the product comprises olefin or olefin-containing polymer.

4. The method of claim 1, wherein the carbon feed comprises methane from natural gas.

5. A method for determining a source of carbon feed used in manufacturing product produced from the carbon feed, comprising:
 providing a feed stream of an oxygenate to an MTO system and contacting the feed stream with an olefin-forming catalyst to form an olefin product;
 providing a sample of the carbon feed;
 directly determining $^{13}C:^{12}C$ ratio of the carbon feed by Laser Induced Florescence (LIF);
 providing a sample of product produced from the carbon feed;
 directly determining $^{13}C:^{12}C$ ratio of the product by Laser Induced Florescence (LIF) without the need to first convert it to $CO_2$ and/or $H_2$; and
 comparing the $^{13}C:^{12}C$ ratio of the product to the $^{13}C:^{12}C$ ratio of the carbon feed from the source.

6. The method of claim 5, further comprising tracking the compared product that falls within a range of from ±5% of the determined carbon feed ratio.

7. The method of claim 6, further comprising sending the tracked product to inventory.

8. The method of claim 5, wherein the product comprises olefin or olefin-containing polymer.

9. A method for determining a source of carbon feed used in manufacturing polymers, comprising:
 providing a feed stream of the oxygenate to an MTO system and contacting the feed stream with an olefin-forming catalyst to form a polyolefin product;
 providing a sample of the carbon feed;
 directly determining $^{13}C:^{12}C$ ratio of the carbon in the feed by Laser Induced Florescence (LIF);
 providing a sample of polyolefin produced from the carbon feed;
 directly determining $^{13}C:^{12}C$ ratio of the polyolefin carbon dioxide by Laser Induced Florescence (LIF) without the need to first convert it to $CO_2$ and/or $H_2$; and
 comparing the $^{13}C:^{12}C$ ratio of the polyolefin to the $^{13}C:^{12}C$ ratio of the carbon in the feed;
 further comprising tracking the compared product that falls within a range of from ±5% of the determined carbon feed ratio from the source.

10. The method of claim 9, further comprising sending the tracked product to inventory.

11. The method of claim 9, wherein the carbon feed comprises methane from natural gas.

* * * * *